(12) United States Patent
Sra

(10) Patent No.: US 7,344,543 B2
(45) Date of Patent: *Mar. 18, 2008

(54) METHOD AND APPARATUS FOR EPICARDIAL LEFT ATRIAL APPENDAGE ISOLATION IN PATIENTS WITH ATRIAL FIBRILLATION

(75) Inventor: Jasbir S. Sra, Pewaukee, WI (US)

(73) Assignee: Medtronic, Inc., Minneapolis, MN (US)

( * ) Notice: Subject to any disclaimer, the term of this patent is extended or adjusted under 35 U.S.C. 154(b) by 501 days.

This patent is subject to a terminal disclaimer.

(21) Appl. No.: 10/882,516

(22) Filed: Jul. 1, 2004

(65) Prior Publication Data

US 2005/0033287 A1    Feb. 10, 2005

Related U.S. Application Data

(60) Provisional application No. 60/531,293, filed on Dec. 19, 2003, provisional application No. 60/484,008, filed on Jul. 1, 2003.

(51) Int. Cl.
*A61B 17/12*    (2006.01)
(52) U.S. Cl. ...................... 606/139; 606/151
(58) Field of Classification Search ............... 606/13, 606/41, 46, 139, 151, 157, 158, 228; 607/119, 607/122; 128/898
See application file for complete search history.

(56) References Cited

U.S. PATENT DOCUMENTS 3,954,098 A    5/1976    Dick et al.
4,574,807 A    3/1986    Hewson et al.
5,245,287 A    9/1993    Nowak et al.
5,274,551 A    12/1993   Corby, Jr.

(Continued)

FOREIGN PATENT DOCUMENTS

EP    1182619 A2    2/2002

(Continued)

OTHER PUBLICATIONS

C.L. Grines et al.; "Functional Abnormalities in Isolated Left Bundle Branch Block: The Effect of Interventricular Asynchrony;" *Circulation*; 1989; 79:845-53.

(Continued)

*Primary Examiner*—A. Farah
(74) *Attorney, Agent, or Firm*—Jansson Shupe & Munger Ltd.

(57) ABSTRACT

A catheter apparatus is provided for isolation of the left atrial appendage (LAA) having a catheter shaft, a probe disposed within the catheter shaft, and a control mechanism coupled to both the catheter shaft and the probe. The catheter shaft includes a main body with a distal tip section. The tip section can be deflected from the shaft's central axis in a controlled manner. The probe can be extended outward from the catheter shaft and has a distal end that is brought into contact with the LAA. The control mechanism controls the catheter shaft's rotational and longitudinal movement, the tip section's degree of deflection, and the probe's axial movement with respect to the catheter shaft. Preferably, the distal end is able to form a pre-stressed loop selected to have a size allowing it to substantially encircle the LAA's base. A method for epicardial isolation of the LAA is also provided.

19 Claims, 7 Drawing Sheets

U.S. PATENT DOCUMENTS

| | | | |
|---|---|---|---|
| 5,304,212 A | 4/1994 | Czeisler et al. | |
| 5,348,020 A | 9/1994 | Huston | |
| 5,353,795 A | 10/1994 | Souza et al. | |
| 5,391,199 A | 2/1995 | Ben-Haim | |
| 5,431,688 A | 7/1995 | Freeman | |
| 5,464,447 A | 11/1995 | Fogarty et al. | |
| 5,568,384 A | 10/1996 | Robb et al. | |
| 5,738,096 A | 4/1998 | Ben-Haim | |
| 5,823,958 A | 10/1998 | Truppe | |
| 5,829,447 A | 11/1998 | Stevens et al. | |
| 5,839,440 A | 11/1998 | Liou et al. | |
| 5,846,254 A | 12/1998 | Schulze et al. | |
| 5,871,532 A | 2/1999 | Schroeppel | |
| 5,951,475 A | 9/1999 | Gueziec et al. | |
| 5,954,692 A | 9/1999 | Smith et al. | |
| 6,079,414 A | 6/2000 | Roth | |
| 6,081,577 A | 6/2000 | Webber | |
| 6,154,516 A | 11/2000 | Heuscher et al. | |
| 6,161,543 A * | 12/2000 | Cox et al. | 128/898 |
| 6,233,304 B1 | 5/2001 | Hu et al. | |
| 6,234,804 B1 | 5/2001 | Yong | |
| 6,235,038 B1 | 5/2001 | Hunter et al. | |
| 6,249,693 B1 | 6/2001 | Cline et al. | |
| 6,252,924 B1 | 6/2001 | Davantes et al. | |
| 6,254,568 B1 | 7/2001 | Ponzi | |
| 6,256,368 B1 | 7/2001 | Hsieh et al. | |
| 6,266,553 B1 | 7/2001 | Fluhrer et al. | |
| 6,289,115 B1 | 9/2001 | Takeo | |
| 6,289,239 B1 | 9/2001 | Panescu et al. | |
| 6,311,693 B1 | 11/2001 | Sterman et al. | |
| 6,314,310 B1 | 11/2001 | Ben-Haim et al. | |
| 6,325,797 B1 | 12/2001 | Stewart et al. | |
| 6,348,034 B1 | 2/2002 | Thompson | |
| 6,348,793 B1 | 2/2002 | Balloni et al. | |
| 6,350,248 B1 | 2/2002 | Knudson et al. | |
| 6,353,445 B1 | 3/2002 | Babula et al. | |
| 6,381,485 B1 | 4/2002 | Hunter et al. | |
| 6,389,104 B1 | 5/2002 | Bani-Hashemi et al. | |
| 6,394,948 B1 | 5/2002 | Brost et al. | |
| 6,401,720 B1 | 6/2002 | Stevens et al. | |
| 6,411,848 B2 | 6/2002 | Kramer et al. | |
| 6,421,412 B1 | 7/2002 | Hsieh et al. | |
| 6,423,051 B1 | 7/2002 | Kaplan et al. | |
| 6,456,867 B2 | 9/2002 | Reisfeld | |
| 6,468,265 B1 | 10/2002 | Evans et al. | |
| 6,478,028 B1 | 11/2002 | Paolitto et al. | |
| 6,478,803 B1 | 11/2002 | Kapec et al. | |
| 6,484,727 B1 * | 11/2002 | Vaska et al. | 128/898 |
| 6,490,475 B1 | 12/2002 | Seeley et al. | |
| 6,490,479 B2 | 12/2002 | Bock | |
| 6,520,953 B1 | 2/2003 | Schultz | |
| 6,549,606 B1 | 4/2003 | Vaillant et al. | |
| 6,556,695 B1 | 4/2003 | Packer et al. | |
| 6,579,285 B2 * | 6/2003 | Sinofsky | 606/16 |
| 6,584,343 B1 | 6/2003 | Ransbury et al. | |
| 6,606,113 B2 | 8/2003 | Nakamura | |
| 6,612,980 B2 | 9/2003 | Chen et al. | |
| 6,614,595 B2 | 9/2003 | Igarashi | |
| 6,628,976 B1 | 9/2003 | Fuimaono et al. | |
| 6,650,927 B1 | 11/2003 | Keidar | |
| 6,711,428 B2 | 3/2004 | Fuimaono et al. | |
| 6,733,499 B2 | 5/2004 | Scheib | |
| 6,782,284 B1 | 8/2004 | Subramanyan et al. | |
| 6,795,721 B2 | 9/2004 | Coleman et al. | |
| 6,805,128 B1 * | 10/2004 | Pless et al. | 128/898 |
| 6,858,026 B2 * | 2/2005 | Sliwa et al. | 606/28 |
| 6,926,714 B1 * | 8/2005 | Sra | 606/41 |
| 6,942,661 B2 * | 9/2005 | Swanson | 606/41 |
| 7,052,493 B2 * | 5/2006 | Vaska et al. | 606/41 |
| 7,089,063 B2 * | 8/2006 | Lesh et al. | 607/101 |
| 2002/0010392 A1 | 1/2002 | Desai | |
| 2002/0046756 A1 | 4/2002 | Laizzo et al. | |
| 2002/0138105 A1 | 9/2002 | Kralik | |
| 2003/0018251 A1 | 1/2003 | Solomon | |
| 2003/0023266 A1 | 1/2003 | Borillo et al. | |
| 2003/0028183 A1 | 2/2003 | Sanchez et al. | |
| 2003/0097219 A1 | 5/2003 | O'Donnell et al. | |
| 2003/0187358 A1 | 10/2003 | Okerlund et al. | |
| 2003/0220557 A1 | 11/2003 | Cleary et al. | |
| 2004/0087850 A1 | 5/2004 | Okerlund et al. | |
| 2004/0225212 A1 | 11/2004 | Okerlund et al. | |
| 2004/0225328 A1 | 11/2004 | Okerlund et al. | |
| 2004/0225331 A1 | 11/2004 | Okerlund et al. | |
| 2005/0038333 A1 * | 2/2005 | Sra | 600/374 |
| 2005/0273090 A1 * | 12/2005 | Nieman et al. | 606/15 |

FOREIGN PATENT DOCUMENTS

| | | |
|---|---|---|
| EP | 1321101 A2 | 12/2002 |
| WO | WO 91/07726 | 5/1991 |
| WO | WO 96/10949 | 4/1996 |

OTHER PUBLICATIONS

H.B. Xia et al., "Differing effects of right ventricular pacing and left bundle branch block on left ventricular function;" *Br. Heart J.*, 1993; 69:166-73.

S. Cazeau et al., "Effects of Multisite Biventricular Pacing in Patients with Heart Failure and Intraventricular Conduction Delay;" *N. Engl. J. Med.* 2001; 344:873-880.

M.V. Pitzalls et al., "Cardiac Resynchronization Therapy Tailored by Echocardiographic Evaluation of Ventricular Acnchrony;" *J. Am. Coll. Cardiol.* 2002; 40:1615-22.

W.T. Abraham et al., "Cardiac Resynchronization in Chronic Heart Failure;" *N. Engl. J. Med.* 2002; 346:1845-1853.

W.M. Feinberg et al.; "Prevalence, Age Distribution, and Gender of Patients with Atrial Fibrillation;" *Arch. Intern. Med.* vol. 155; Mar. 1995; pp. 469-473.

J.L. Cox, J.P. Boineau, R.B. Schuessler, T.B. Ferguson, Jr., M.E. Cain, B.D. Lindsay, P.B. Corr, K.M. Kater, D.G. Lappas; "Operations for Atrial Fibrillation;" Electrophysiology, Pacing and Arrhythmia, Clin. Cardiol. 14, 1991; pp. 827-834.

M.Haissaguerre, P. Jais, S.C. Shah, A. Takahashi, M. Hocini, G. Quiniou, S. Garrigue, A. LeMouroux, P. Le Metayer, and J. Clementy; "Spontaneous Initiation of Atrial Fibrillation by Ectopic Beats Originating in the Pulmonary Viens;" The New England Journal of Medicine, vol. 339, No. 10, Sep. 3, 1998; pp. 659-668.

C. Pappone, S. Rosanio, G. Augello, G. Gallus, G. Vicedomini, P. Mazzone, S. Gulletta, F. Gugliotta, A. Pppone, V. Santinelli, V. Tortoriello, S. Sal, A. Zangrillo, G. Crescenzi, S. Benussi, and O. Alfieri; "Mortality, Morbidity, and Quality of Life After Circumferential Pulmonary Vein Ablation for Atrial Fibrillation;" Journal of the American College of Cardiology, vol. 42, No. 2; 2003; 185-197.

J. Sra et al., "Current Problems in Cardiology—Atrial Fibrilliation: Epidemiology, Mechanisms, and Management;" Current Problems in Cardiology, Jul. 2000; pp. 406-524.

ACC/AHA/ESC Practise Guidelines; Eur. Heart J., vol. 22, issue 20, Oct. 2001; pp. 1854-1923.

M.D. Leash, T. Trepelse, H. Omran, A. Bartorelli, P. Della Bella, T. Nakai, M. Reisman, D. Fleschenberb, U. Krumsdorf, and D. Scherer; "Tiny Device Blocks 'Usless' Part of Heart, prevents blood clots;" Journal Report; American Heart Association; Apr. 9, 2002.

Ellen Barlow; "Operating in 3-D" found at www.med.harvard.edu/publications/HMAB/196fo3d.html.

H. Nikagawa et al., "Role of the Tricuspid Annulus and the Eustachian Valve/Ridge on Atrial Flutter: Relevance to Catheter Ablation of the Septal Isthmus and a New Technique for Rapid Identification of Ablation Success;" *Circulation* 1996; 94:407-24.

L. Gepstein et al., "A Novel Method for Nonfluoroscopic Catheter-Based Electroanatomical Mapping of the Heart: In Vitro and In Vivo Accuracy Results;" *Circulation* 1997; 95:1611-22.

S.Shpun et al., "Guidance of Radiofrequency Endocardial Ablation with Real-time Three-dimensional Magnetic Navigation System;" *Circulation* 1997; 96:2016-21.

J. Sra et al., "Electroanatomic Mapping to Identify Breakthrough Sites in Recurrent Typical Human Flutter;" *Paceing Clin. Electrophysiol* 2000: 23:1479-92.

R.J. Schilling et al.; "Simultaneous Endocardial Mapping in the Human Left Ventricle Using a Noncontact Catheter: Comparison of Contact and Reconstructed Electrograms During Sinus Thythm;" *Circulation* 1998; 98:997-98.

C.C. Gornick et al., "Validation of a New Noncontact Catheter System for Electroanatomic Mapping of Left Ventricular Endocardium;" *Circulation* 1999; 99:829-835.

J. Sra et al., "Noncontact Mapping for Radiofrequency Ablation of Complex Cardiac Arrhythmias;" *J. Interven. Cardiac Electrophysiol* 2001; 5:323-331.

N. M.S. de Groot et al., "Three-Dimensional Catheter Positioning During Radiofrequency Ablation in Patients: First Application of a Real-Time Position Management System;" *J. Interven. Cardiac Electgrophysiol* 2001; Nov. 11(11):1183-92.

J. Schreieck et al., "Radiofrequency Ablation of Cardiac Arrhythmias Using a Three-Dimensional Real-Time Position Management and Mapping System;" *Pacing Clin. Electrophysiol*, Dec. 2002, 25(12):1699-707.

F. Wittkampf et al., "Real-Time, Three-Dimensioanl, Nonfluoroscopic Localization of the Lasso Catheter;" *J Interven. Cardiac Electrophysiol*, 2002, 13:630.

J. Sra et al., "Cardiac Chamber Geometry Construction, Catheter Navication and Ablation Using Cutaneous Patches;" *Supplement to Circulation* Oct. 2003, 108 (17):IV-585, Abstract 2667.

J. Sra et al., "Three-Dimensional Right Atrial Geometry Construction and Catheter Tracking Using Cutaneous Patches;" *J. Interven. Cardiac Electrophysiol*, 2003 14: 897.

Z. Zhang; "Iterative Point Matching for Regitration of Free-Form Curves;" *Inria* 1992, pp. 1-40.

C.A. Pelizzari et al., "Accurate Three-Dimensional Registration of CT, PET, and/or MR Images of the Brain;" *J. Comput. Assist. Tomogr.* 1989; 13:20-26.

A.C. Evans et al.; "MRI-PET Correlation in Three Dimensions Using a Volume-of-Interest (VOI) Atlas;" *J. Cerb Flow Metab.* 1991; 11:A69-A78.

R.P. Woods et al.; "Rapid Automated Algorithm for Aligning and Reslicing PET Images;" *Journal of Computer Assisted Tomography*, 1992; 16:620-633.

B.A. Ardekani et al.; "A Fully Automatic Multimodality Image Registration Algorithm;" *Journal of Computer Assisted Tomography*; 1995; 19:615-623.

L. Thurfell et al.; "Registration of Neuroimaging Data: Implementation and Clinic Applications;" *American Society of Neuroimaging*; 2000; 10:39-46.

S.A. Ben-Haim et al.; "Nonfluoroscopic, in vivo navigation and mapping technology;" *Nature Medicine*; 1996, 2:1393-5.

B. Taccardi et al.; "A new intracaitary probe for detecting the site of origin of ectopic ventricular beats during one cardiac cycle;" *Circulation*; 1987; 75:272-81.

F.H.M. Wittkampf et al.; "New Technique for Real-Time 3-Dimensional Localization of Regular Intracardiac Electrodes;" *Circulation*; 1999; 99:1312-17.

V. Fuster et al. "ACC/AHA/NASPE 2002 Guidelines Update for Implantation of Pacemakers and Antiarrhythmia Devices;" *J. Am. Coll. Cardiol* 2001; 38:1-47.

D. R. Ney "Volumetric Rendering of Computed Tomography Data: Principles and Techniques;" *IEEE Computer Graphics and Application*; 1990; 24-32.

N. M. Alpert et al., "The Principal Axes Transformation—A Method for Image Registration;" *The Journal of Nuclear Medicine*; 1990; 31:1717-1722.

P.A. van den Elsen et al., "Medical Image Matching—A Review with Classification;" *IEEE Engineering in Medicine and Biology*, 1993; 26-38.

G. T. Barnes et al.; "Conventional and Spiral Computed Tomography: Physical Principles and Image Quality Considerations;" *Computed Body Tomography*, 1998, Lippincot-Raven, Philadelphia, PA pp. 1-20.

Milan Sonka and J. Michael Fitzpatrick (eds); *Handbook of Medical Imaging* vol. 2. *Medical Image Processing and Analysis*; pp. 129-174 & 447-506.

"Advanced Vessel Analysis" prouct description [online] http://www.gehealthcare.com/usen/ct/clin_app/products/aswessel.html [retrieved Dec. 1, 2004].

"CardilQ" product description [online], http://egems.gehealthcare.com/geCommunity/Europe/flex_trial/awFlexTrial/aw3_1/eflextrial [retrieved Dec. 1, 2004].

"Current Problems in Cardiology—Atrial Fibrillation: Epidemiology, Mechanisms, and Management;" Current Problems in Cardiology, Jul. 2000; pp. 406-524.

Jasbir Sra, M.D., F.A.C.C. "Synchronized Registration of Three-Dimensioanl Left Atrial Computerized Tomographic Images with Cardiac Mapping: Validation of Registration Procedure", *Circulation*,vol. 108, No. 17, Oct. 28, 2003.

Jasbir Sra, M.D. "Synchronized Registration of Three-Dimensional Left Atrial Images in Atrial Fibrillation", *Pacing And Clinical Electgrophysiology*, Apr. 2003, vol. 26, No. 4, Part II, pp. 929-1173.

PCT Search Report for PCT/US2004/020909.

\* cited by examiner

METHOD AND APPARATUS FOR EPICARDIAL LEFT ATRIAL APPENDAGE ISOLATION IN PATIENTS WITH ATRIAL FIBRILLATION

RELATED APPLICATION

This application claims the benefit of U.S. Provisional Application No. 60/484,008, filed on Jul. 1, 2003 and U.S. Provisional Application No. 60/531,293 filed on Dec. 19, 2003.

FIELD OF THE INVENTION

This invention relates generally to catheter apparatus for cardiac interventional treatment and, in particular, to catheter apparatus for isolation of the left atrial appendage (LAA) in patients with atrial fibrillation (AF).

BACKGROUND OF THE INVENTION

Atrial fibrillation (AF), a heart rhythm problem in which the atria (upper chambers of the heart) stop contracting as they fibrillate or quiver, is the most common of all the heart rhythm problems. It is estimated that over 2.2 million patients in the U.S. have AF and over 140,000 new cases are diagnosed every year. Patients with AF have a high risk of stroke. The Framingham Study demonstrated that the diagnosis of AF increased the risk of stroke 3 to 5 times higher and the risk rose from 1.5 percent during the fifth decade of life to over 23% by the eight decade.

More specifically, previous studies have indicated that more than 90 percent of AF related strokes result from a blood clot that forms in the left atrial appendage (LAA), a small pouch-like structure in the left atrium. Such blood clots can dislodge from the atrium and travel to the brain, thereby causing a stroke. Several large trials have shown the efficacy of warfarin, a blood thinner, in reducing the risk of stroke. In clinical practice, however, the warfarin is contraindicated or cannot be used because of side effects such as bleeding in over 40 percent of patients.

In addition to the LAA being a source of blood clots it can also play a role in the initiation and maintenance of AF. In treating AF, lesions are placed at strategic locations to prevent the conduction of errant electrical impulses. The LAA appendage is routinely removed in a surgical procedure for treating AF called the MAZE procedure. The removal of the LAA has been recommended by the American College of Cardiology-American Heart Association guidelines.

Recently, a catheter technique call PLAATO (percutaneous left atrial appendage trans catheter occlusion) has been tried as a blocking device from the inside of the left atrial chamber. In one study of this technique, the catheter implant sizes ranged significantly, the procedure time ran over 90 minutes and, in 25 percent of these patients, the initial device required removal and replacement with a device of a different size. There was also additional risk of bleeding around the heart, a complication that can at times be life-threatening.

There is thus a need for a method and system for establishing an effective road map of the LAA. There is also a need for a method and system for isolating the LAA that uses a minimally-invasive approach not going inside the left atrial chamber. Such a method and system would eliminate the need for different size catheters and reduce the risk of complications, thereby providing an alternative strategy for the prevention of stroke and the treatment of AF.

It is an object of this invention to provide an improved catheter apparatus for use in the isolation of the LAA that overcomes some of the problems and shortcomings in the prior art, including those referred to above.

SUMMARY OF THE INVENTION

This invention is for a catheter apparatus used in the isolation of a patient's left atrial appendage (LAA) having a catheter shaft, a probe axially disposed within the catheter shaft, and a control mechanism coupled to both the catheter shaft and the probe. The catheter shaft includes a main body that extends along a central axis and a coaxial tip section attached to the main body. The tip section can be deflected from the central axis in a controlled manner. The probe can be extended outward from the catheter shaft and has a distal end that is brought into contact with the LAA. The control mechanism controls longitudinal movement of the catheter shaft, the degree of deflection of the tip section, and axial movement of the probe with respect to the catheter shaft.

In one desirable embodiment, the catheter shaft can be rotated about its central axis. More desirable is where the distal end has a pre-stressed curve so that the distal end curves as the probe is extended outward from the catheter shaft. In such embodiments, the distal end preferably includes a saline. Most preferred is where the saline is fabricated from nickel-titanium where the alloy has shape memory.

One very preferred embodiment finds the distal end able to form a loop when the probe is fully extended from the catheter shaft. This loop is selected to have a size that will allow it to substantially encircle the base of the LAA. In certain desirable cases, the loop is substantially perpendicular to the axis of the catheter shaft. In other preferred cases, the loop is coplanar with this axis.

Another preferred embodiment is where the control mechanism is a steering handle. More desirable is where the steering handle includes a first actuator that is mechanically connected to the catheter shaft to control its rotation and axial movement. Most preferred is where the steering handle also includes a second actuator mechanically connected to the shaft's tip section to control the deflection of the tip section. It is highly preferred where the steering handle has a third actuator that is mechanically connected to the probe and that controls the axial movement of the probe within the catheter shaft.

One very highly desired embodiment finds the steering handle having a fourth actuator. This control is mechanically connected to a proximal coil on the probe and it enables the distal end to be disengaged from the probe at the point of this proximal coil.

In another aspect of this invention, it provides a method for isolating the LAA on a patient. This method includes the steps of introducing a catheter apparatus through an incision in the patient's chest, navigating the catheter apparatus to the LAA, and using the catheter apparatus to isolate the LAA. The catheter apparatus is preferably one that includes: (1) a catheter shaft having a main body that is rotatable about its central axis and having a coaxial tip section that can be selectively curved away from the central axis; (2) a probe slidably disposed within the catheter shaft that can be extended outward from the shaft and having a distal end with a pre-stressed curve that takes the shape of the curve when the distal end protrudes from the catheter shaft; and (3) a steering handle coupled to the catheter shaft and the probe where the steering handle is capable of controlling the rotation and axial movement of the catheter shaft, the deflection of the tip section, and the axial movement of the probe within the catheter shaft.

In certain desirable cases, the distal end includes a saline. More desirable is where the curve of the distal end forms a loop when the probe is fully extended from the catheter shaft. This loop is sized to be able to circumscribe the base of the LAA and is oriented in a plane substantially perpendicular to the central axis. Highly preferred is where the steering handle is also mechanically connected to a proximal coil on the probe so that it can control the disengagement of the distal end from the probe at this proximal coil.

DETAILED DESCRIPTION OF PREFERRED EMBODIMENTS

Figure 1:
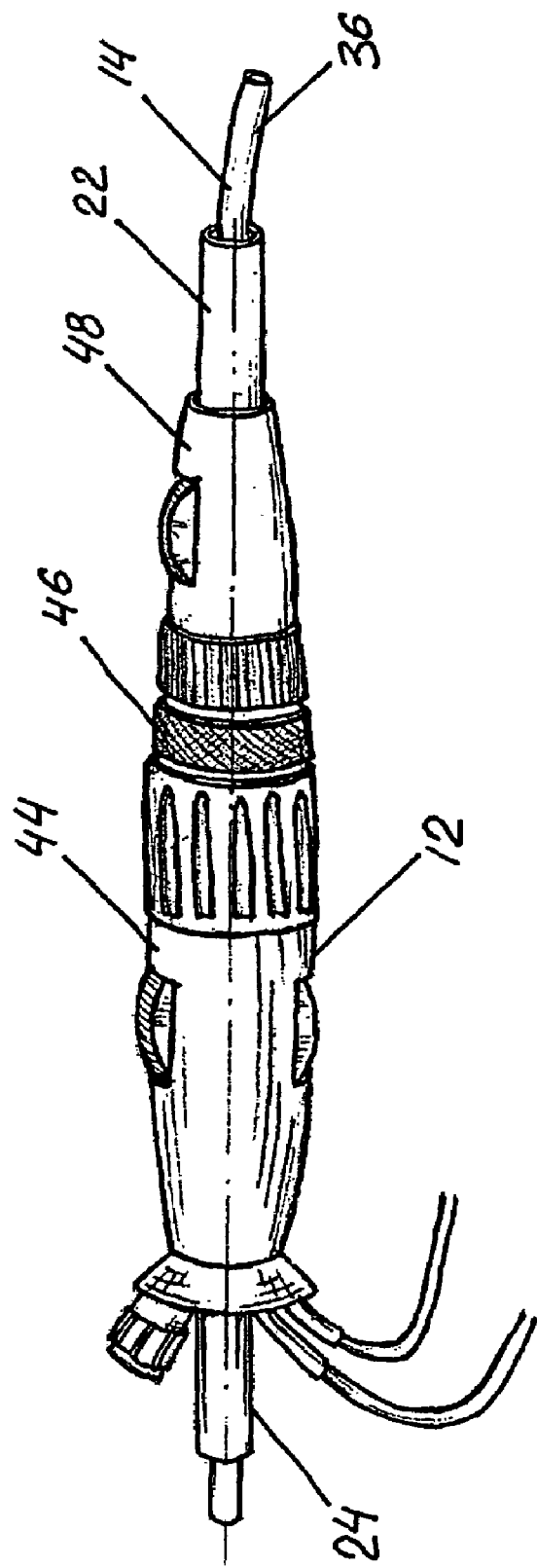
FIG. 1 is a perspective view of a preferred catheter apparatus for use in the isolation of the left atrial appendage (LAA) in accordance with this invention having the tip section of the catheter shaft deflected.
Figure 2:
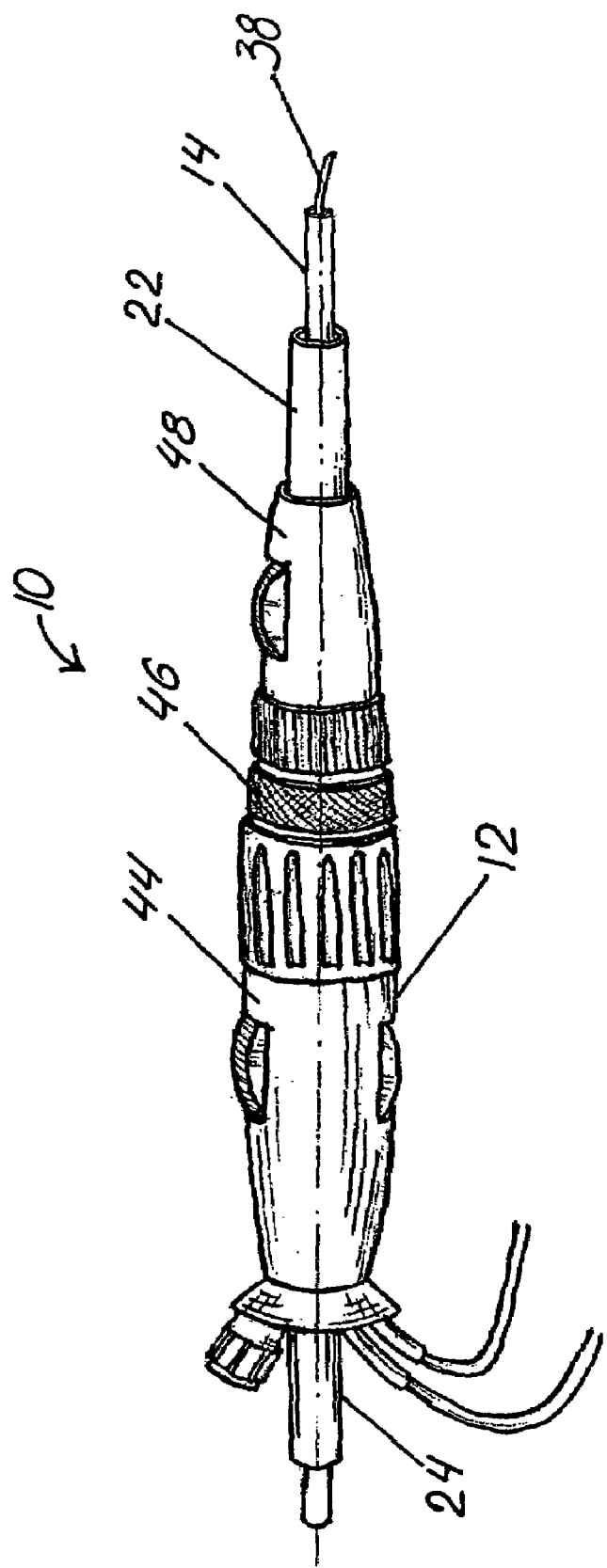
FIG. 2 is a perspective view of the apparatus of FIG. 1 having the probe partially extending from the catheter shaft.

Referring to FIGS. 1-4, a catheter apparatus 10 in accordance with this invention is shown that enables an electrophysiologist, cardiologist and/or surgeon to isolate the left atrial appendage (LAA). The catheter apparatus 10 is preferably an endoscopic or thoracoscopic delivery system having a steering handle 12, a catheter shaft 14, and a probe 16. Steering handle 12 is hollow and has a front end 18 and a rear end 20. A hollow introducer tube 22 extends from the front end 18. Introducer tube 22 is preferably formed from a rigid material such that introducer tube 22 can be inserted through an incision in a patient. A hollow extended tube 24 extends from the rear end 20. Introducer tube 22, steering handle 12 and extended tube 24 are coaxial with each other along central axis 25, thereby defining a continuous central opening 26.

Rear end 20 includes apertures to receive both a light source 28 and a camera 30. Light source 28 and camera 30 are fed through introducer tube 22 to forward aperture 32. Light source 28 and camera 30 allow images to be displayed in real-time through a display device such as a video monitor so that the physician may monitor the procedure being performed. Rear end 20 of steering handle 12 also receives an irrigation port 34 that is connected to a supply of irrigation fluid to assist in irrigating and aspirating catheter apparatus 10 as needed.

Central opening 26 is sized to receive catheter shaft 14. Catheter shaft 14 is introduced through extended tube 24 so that catheter shaft 14 can extend outward from forward aperture 32 of introducer tube 22. Catheter shaft 14 has a hollow, open interior and is sized to receive probe 16. The diameter of catheter shaft 14 is not critical but 8 French is preferred. Catheter shaft 14 is preferably made from polyurethane. Nylon can be added to increase the strength of catheter shaft 14 while flexibility at its tip section 36 can be achieved by eliminating or reducing the amount of stiffening material. Two sets of non-conducting wires (not shown) are anchored to the inside of the catheter shaft by thermal bonding to add further strength. These wires can be made from a nickel-titanium alloy such as nitinol or from steel.

Probe 16 is positioned within catheter shaft 14 where probe 16 is free to move forward and backward along the longitudinal axis of catheter shaft 14. The length of probe 16 can be selected based on the size, orientation or other anomalies of the LAA. The diameter of probe 16 is also not critical but 6 French is preferred.

Figure 3:
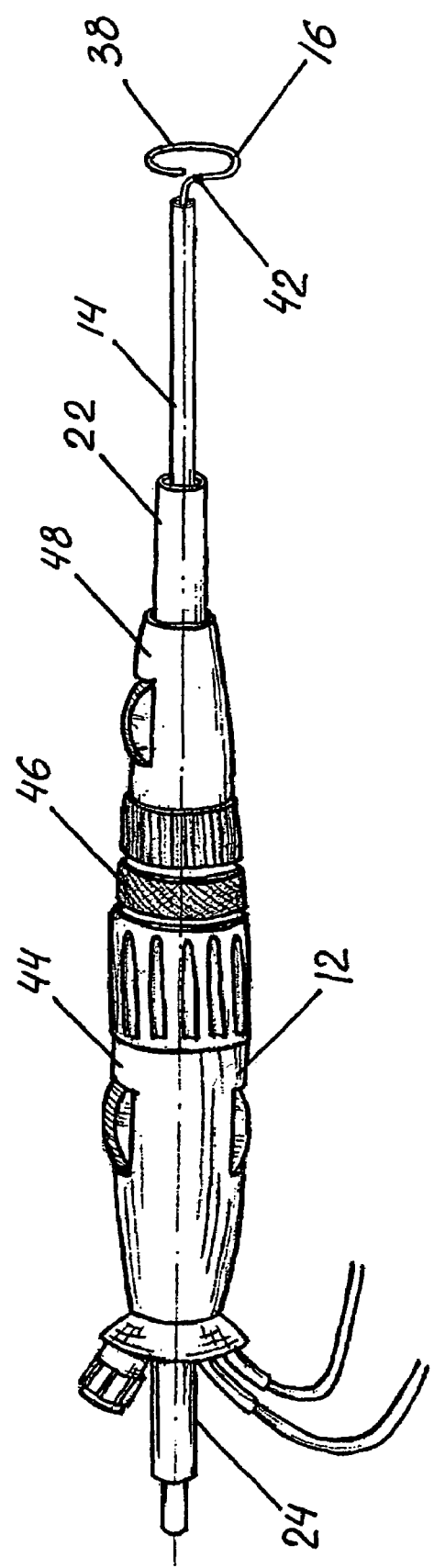
FIG. 3 is a perspective view of the apparatus of FIG. 1 having the probe form a loop perpendicular to the catheter shaft.
Figure 4:
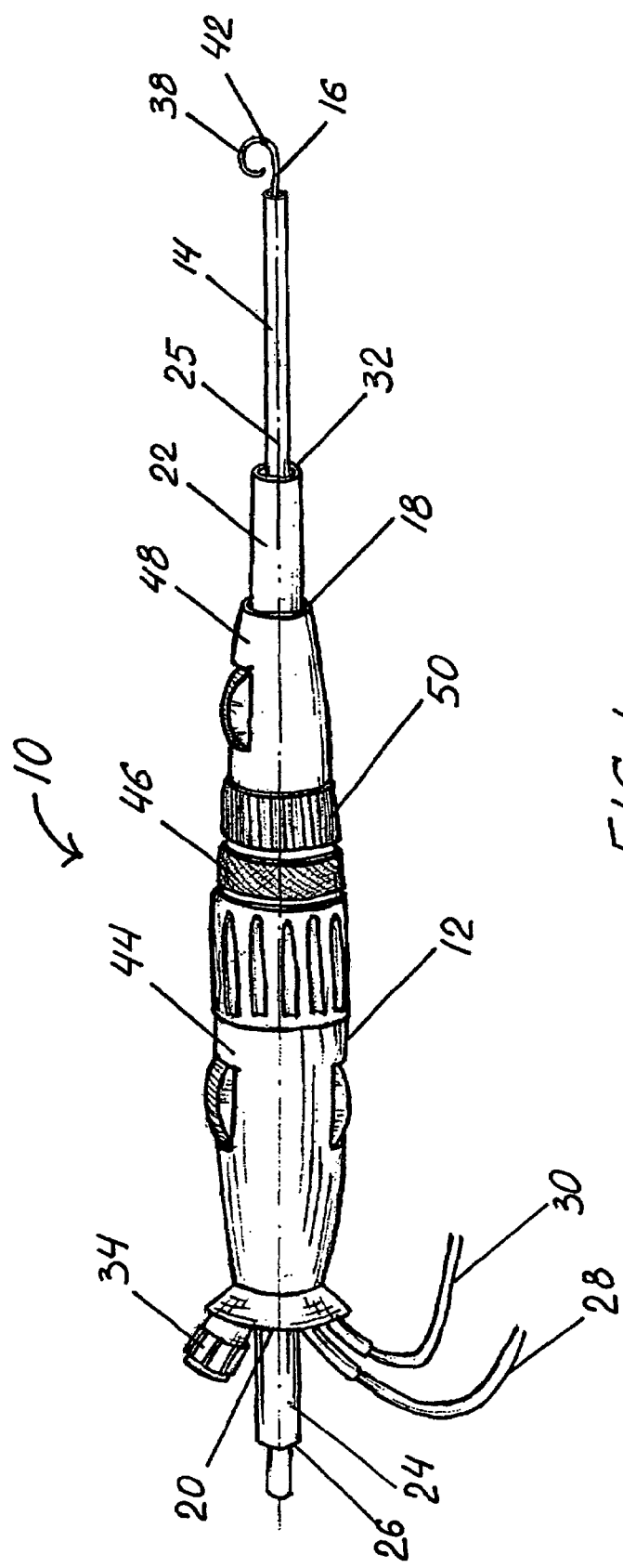
FIG. 4 is a perspective view of the apparatus of FIG. 1 having the probe form a loop coplanar with the catheter shaft.
Figure 5:
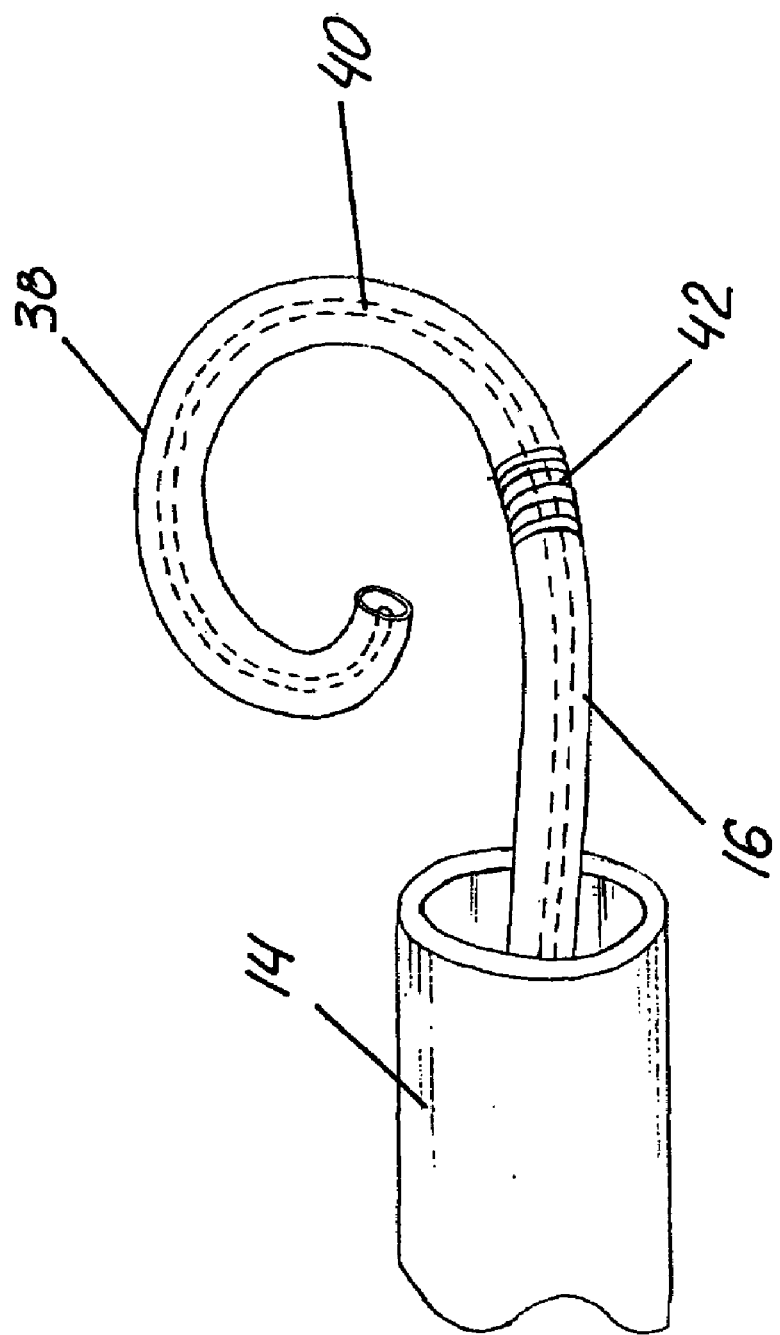
FIG. 5 is an enlarged view of a probe in accordance with this invention with the saline positioned therein.

As probe 16 protrudes from catheter shaft 14, distal end 38 of probe 16 achieves a pre-stressed curve as shown in FIGS. 2-5. The pre-stressed curve is designed to make a tight fit around the base of the LAA. It is anticipated that several different sizes may be needed depending upon the size of the LAA. The pre-stressed curve of distal end 38 is achieved by using an elongated member or saline 40 as illustrated in FIG. 5. Saline 40 is positioned inside the body of probe 16 and the distal end of saline 40 is formed to achieve different pre-stressed curves. Saline 40 is preferably composed of inert wires fabricated from a nickel-titanium alloy having shape memory as, for example, nitinol. The cross-sectional area of saline 40 in the pre-stressed curve location may be thinner compared to the rest of saline 40.

As shown in FIG. 5, probe 16 further includes proximal coil 42. Proximal coil 42 is made from several non-conducting wires and encircles the outside circumference of probe 16. Proximal coil 42 abuts distal end 38 and serves to achieve disengagement of distal end 38 from the remainder of probe 16 as will be described in detail below.

Steering handle 12 is provided with four actuators 44, 46, 48, 50. First actuator 44 is mechanically connected to catheter shaft 14 by non-conducting wire in a manner known to those skilled in the art that gives control over the axial and rotational movement of catheter shaft 14. Second actuator 46 controls angled movement of tip section 36. Tip section 36 is preferably the distal 1 cm. of catheter shaft 14. Second actuator 46 is mechanically connected to tip section 36 to allow tip section 36 to deflect away from central axis 25 as second actuator 46 is rotated. The degree of deflection available is preferably 30 to 60°. Selective adjustment of the longitudinal, rotational, and angular position of catheter shaft 14 permits catheter apparatus 10 to accommodate different sizes and orientations of LAA.

Third actuator 48 is attached by non-conducting wire to probe 16. Third actuator 48 controls forward and backward movement of probe 16 within catheter shaft 14. Fourth actuator 50 is joined by non-conducting wire to proximal coil 42. Rotation of fourth actuator 50 in a clockwise direction places tension upon proximal coil 42 to snap or break off the distal portion of probe 16 forward of proximal coil 42.

The procedure for isolating the LAA using catheter apparatus 10 will now be described. Initially, the patient is positioned in a supine position and a double lumen endotracheal tube is inserted to ventilate the right lung while, at the same time, ventilation is blocked to the left lung so as to create a space in the left pleural cavity. With the left lung deflated, a small incision is made upon the chest to permit one of two approaches that can be used to deliver probe 16 to the LAA site. These approaches will be discussed in more detail below.

A small 4-5 mm. by 3-4 cm. thoracic port is placed over the incision and anchored in place. The thoracic port helps maintain the intercostal space, decreases trauma and maintains pleural access. Introducer tube 22 is inserted through the thoracic port allowing light source 28 and camera 30 to be used to verify lack of left lung ventilation, to identify intrapleural and mediastinal anatomies, and to navigate catheter shaft 14 and probe 16 to the LAA.

Once the introducer tube 22 is properly positioned, catheter shaft 14 is advanced outward from tube 22 until catheter shaft is positioned adjacent to the base of the LAA. There are two approaches that can be used to deliver probe 16 to the LAA site. In the first approach, catheter shaft 14 and probe 16 are introduced using the subxiphoid approach. Probe 16 can be extended from catheter shaft 14 to form a pre-stressed circular loop coplanar with the axis of catheter shaft 14 as shown in FIG. 4 when introduced in this fashion.

Figure 6:
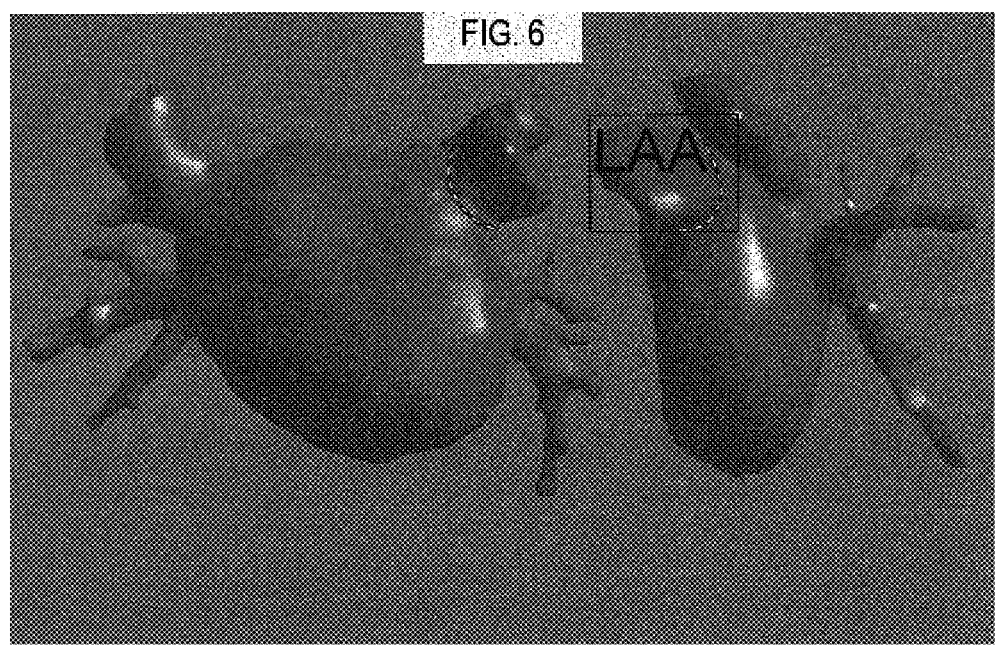
FIG. 6 depicts a probe positioned around an imaged LAA in accordance with this invention.

In the second approach, a small incision is made in the left chest area. In this approach, probe 16 comes out from catheter shaft 14 to form a pre-stressed circular loop at a right angle to the axis of catheter shaft 14 as illustrated in FIG. 3. In either approach, catheter shaft 14 has been positioned with respect to the LAA so that as probe 16 moves forward, distal end 38 of probe 16 encircles the base of the LAA. Once distal end 38 has formed a loop and circumscribed the base of the LAA, rotation of fourth actuator 50 in a clockwise direction will separate break the loop from the rest of probe 16 at proximal coil 42. Probe 16 and catheter shaft 14 along with introducer tube 22 are then withdrawn. FIG. 6 depicts an example of a probe 16 encircling the LAA.

Several experiments in the laboratory by the inventor where the LAA had been isolated in animal models without removing it have demonstrated that there are no detrimental effects with this procedure, as no blood clots or other changes were detected during a 6 week follow-up.

Figure 7:
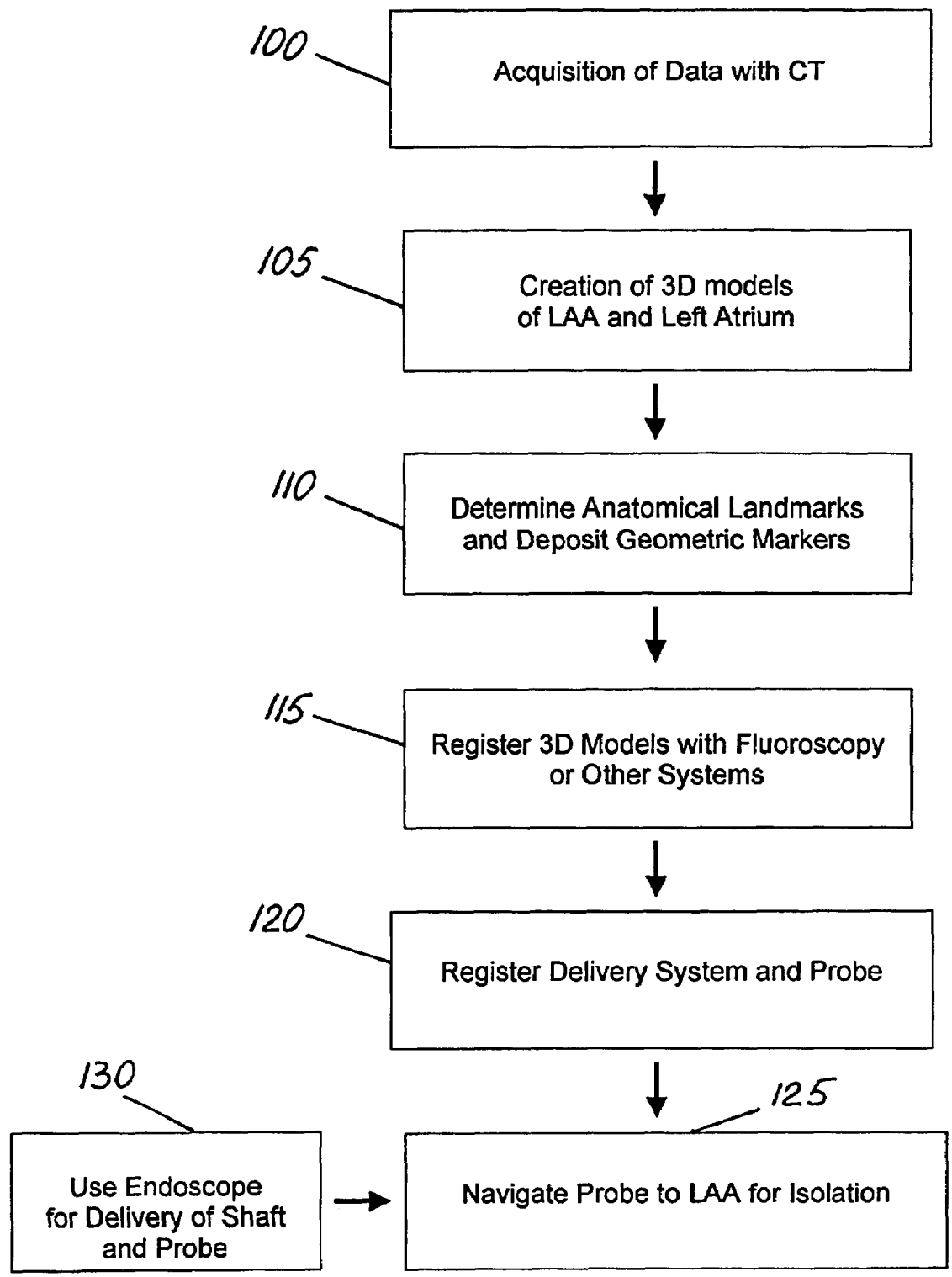
FIG. 7 is a flow diagram of a method for LAA isolation.

FIG. 7 is a flow diagram illustrating a method for LAA isolation. Acquisition and segmentation of left atrium and LAA at step 100 is similar to what has been disclosed in patent application Ser. No. 10/249,812 incorporated herein by reference. A volume of data is acquired on the cardiac CT using a protocol that is optimized for the left atrium and the LAA. The image dataset is segmented with post processing software to extract the surfaces of the heart chambers, including the left atrium and the LAA. The endocardial view (view from inside) can also be visualized to assess the size and orientation of the LAA.

At step 105, the LAA along with the left atrium is visualized using 3D surface and/or volume rendering to create 3D models of the LAA which preferably also include a navigator or endocardial (view from inside) view. Faster scanning speeds can help eliminate the blurring effect seen due to cardiac motion. Another aspect of scanning involves scanning of data which is synchronized with the ECG signal (QRS) in order to produce a graphic representation of the examination volume and thus an image of the heart. The correlation between the scanning data and the ECG signals is fixed so that within each number of successive time intervals a database is obtained.

Anatomical landmarks are identified at step 110. Furthermore, explicit geometric markers are inserted into the volume at landmarks of interest. These markers may be subsequently visualized in a translucent fashion. The saved images are then transferred and registered with the fluoroscopy system and/or the computer workstation of another interventional system as shown at step 115. The orientation, size and any anomalies of the LAA are visualized over the interventional system such that probes of the right size can be selected. The registration process is similar to that detailed in patent application Ser. Nos. 10/063,064 and 60/531,293 incorporated herein by reference. In addition, external markers could be used at the time of registration itself.

In another aspect of the method and system of LAA isolation in patients, as shown at step 120, catheter shaft 14 and probe 16 are visualized on an interventional system such as the fluoroscopy system and/or the computer workstation of another interventional system. Both are visualized as they navigate towards the appendage being isolated at step 125. This delivery system is used to isolate the LAA.

As shown in step 130, the whole process of imaging and registration can be eliminated completely and a catheter apparatus 10, using an endoscopic or thoracoscopic delivery system for example, can position catheter shaft 14 and probe 16 around the LAA using direct visualization in the manner discussed above.

It may be appreciated that automatic techniques may be employed to perform any of the steps by using one or more of the several computer-assisted detection, localization and visualization methods available. Moreover, these methods could be completely automatic or interactive with input from the user. Furthermore, the features described may improve with user input and interaction.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. In particular, although the preceding description discusses LAA imaging and isolation, it is understood that the methodology is not limited to the LAA but may be utilized in other cardiac and non-cardiac applications.

The invention claimed is:

1. A catheter apparatus for use in the isolation of a left atrial appendage (LAA) on a patient comprising:
   a catheter shaft having a central axis and a distal tip section, the tip section being deflectable whereby the tip section can be selectively curved away from the central axis;
   a probe slidably disposed within the catheter shaft, the probe having a distal end and being selectively movable axially within the catheter shaft, whereby the distal end can be extended outward from the catheter shaft and brought into contact with the LAA;
   a handle member sized to slidably receive the catheter shaft; and
   a control mechanism positioned upon the handle member and coupled to the catheter shaft and the probe wherein the control mechanism controls axial movement and deflection of the catheter shaft with respect to the handle member and movement of the probe with respect to the catheter shaft.

2. The apparatus of claim 1 wherein the catheter shaft is rotatable about the central axis.

3. The apparatus of claim 2 wherein the distal end has a pre-stressed curve whereby the distal end curves as the probe is extended from the catheter shaft.

4. The apparatus of claim 3 wherein the distal end includes a spline.

5. The apparatus of claim 4 wherein the saline is fabricated from nickel-titanium having shape memory.

6. The apparatus of claim 3 wherein the distal end forms a loop when the probe is filly extended from the catheter shaft, the loop being sized to substantially circumscribe a base of the LAA.

7. The apparatus of claim 6 wherein the loop substantially defines a plane substantially perpendicular to the central axis.

8. The apparatus of claim 6 wherein the loop is substantially coplanar with the central axis.

9. The apparatus of claim 1 wherein the handle member includes a steering handle and an introducer tube extending outward from a front end of the steering handle.

10. The apparatus of claim 9 wherein the control mechanism is positioned upon the steering handle.

11. The apparatus of claim 10 wherein the control mechanism includes a first actuator mechanically connected with respect to the catheter shaft whereby rotation and axial movement of the catheter shaft is actuated by the first actuator.

12. The apparatus of claim 11 wherein the control mechanism includes a second actuator mechanically connected with respect to the tip section whereby actuation of the second actuator deflects the tip section away from the central axis.

13. The apparatus of claim 12 wherein the control mechanism includes a third actuator mechanically connected with respect to the probe whereby actuation of the third actuator moves the probe axially within the catheter shaft.

14. The apparatus of claim 13 wherein the probe includes a proximal coil and the control in mechanism includes a fourth actuator mechanically connected to the proximal coil whereby actuation of the fourth actuator disengages the distal end from the probe at the proximal coil.

15. A method for epicardial isolation of a left atrial appendage (LAA) on a patient comprising:
   introducing a catheter apparatus through an incision in the patient's chest,
   navigating the catheter apparatus to the LAA;
   advancing a probe from the catheter apparatus;
   substantially circumscribing a base of the LAA with the probe to epicardially isolate the LAA; and
   disengaging a distal end of the probe from the catheter apparatus.

16. The method of claim 15 wherein the catheter apparatus includes:
   a catheter shaft rotatable about a central axis and having a distal tip section, the tip section being deflectable whereby the tip section can be selectively curved away from the central axis;
   the probe slidably disposed within the catheter shaft, the probe being selectively movable axially within the catheter shaft and the distal end having a pre-stressed curve whereby the distal end curves as the probe is extended outward from the catheter shaft;
   a steering handle sized to slidably receive the catheter shaft; and
   a control mechanism positioned upon the steering handle and coupled to both the catheter shaft and the probe wherein the steering handle controls rotation and axial movement of the catheter shaft with respect to the steering handle, deflection of the tip section with respect to the central axis, and movement of the probe with respect to the catheter shaft.

17. The method of claim 16 wherein the distal end includes a spline.

18. The method of claim 17 wherein the curve of the distal end forms a loop when the probe is fully extended from the catheter shaft, the loop being sized to substantially circumscribe a base of the LAA and substantially defining a plane substantially perpendicular to the central axis.

19. The method of claim 18 wherein the probe includes a proximal coil and the control mechanism is mechanically connected to the proximal coil whereby the control mechanism controls disengagement of the distal end from the probe at the proximal coil.

* * * * *

UNITED STATES PATENT AND TRADEMARK OFFICE
CERTIFICATE OF CORRECTION

PATENT NO. : 7,344,543 B2  
APPLICATION NO. : 10/882516  
DATED : March 18, 2008  
INVENTOR(S) : Jasbir S. Sra Page 1 of 1

It is certified that error appears in the above-identified patent and that said Letters Patent is hereby corrected as shown below:

Column 2, line 28, delete "saline" and insert --spline--.  
Column 3, line 5, delete "saline" and insert --spline--.  
Column 3, line 30, delete "saline" and insert --spline--.  
Column 4, line 22, delete "saline" and insert --spline--.  
Column 4, line 23, delete "saline" and insert --spline--.  
Column 4, line 24, delete "saline" and insert --spline--.  
Column 4, line 25, delete "saline" and insert --spline--.  
Column 4, line 28, delete "saline" and insert --spline--.  
Column 4, line 29, delete "saline" and insert --spline--.  
Column 7, line 2, delete "filly" and insert --fully--.

Signed and Sealed this

Seventeenth Day of June, 2008

JON W. DUDAS  
*Director of the United States Patent and Trademark Office*